United States Patent [19]

Mercer

[11] Patent Number: 5,108,840
[45] Date of Patent: Apr. 28, 1992

[54] MULTILAYER ELECTRONIC CIRCUIT ARTICLE HAVING A POLY(NAPHTHYL ETHER) DIELECTRIC

[75] Inventor: Frank Mercer, Belmont, Calif.

[73] Assignee: Raychem Corporation, Menlo Park, Calif.

[21] Appl. No.: 447,771

[22] Filed: Dec. 8, 1989

[51] Int. Cl.$^5$ .................. B32B 9/04; C08G 63/18
[52] U.S. Cl. .................. 428/411.1; 428/419; 428/441; 428/451; 428/461; 361/386; 427/108; 528/125
[58] Field of Search .................. 428/411.1, 419, 441, 428/451

[56] References Cited
FOREIGN PATENT DOCUMENTS
0282096A2  9/1988  European Pat. Off. .
2224648  5/1971  Fed. Rep. of Germany .

*Primary Examiner*—P. C. Sluby
*Attorney, Agent, or Firm*—Yuan Chao; Herbert G. Burkard

[57] ABSTRACT

A fluorinated poly(naphthyl ether) having a repeat unit of the formula

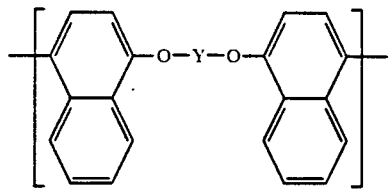

wherein Y is $(CF_2)_m$,

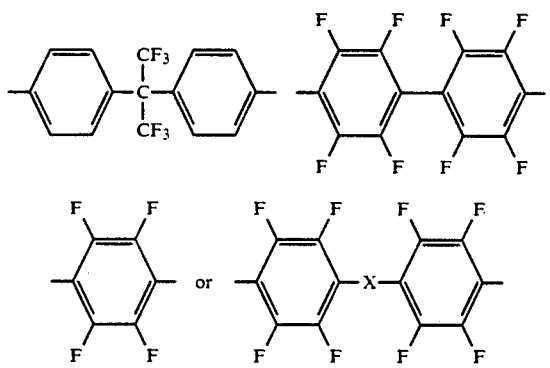

m is an integer from 1 to 4, inclusive, and X is S, CO, $SO_2$, O, $P(C_6H_5)$, or C(OH)H. Such polymers are useful as low dielectric constant, low moisture absorption insulators for multilayered integrated circuit articles, especially in their crosslinked form.

9 Claims, 2 Drawing Sheets

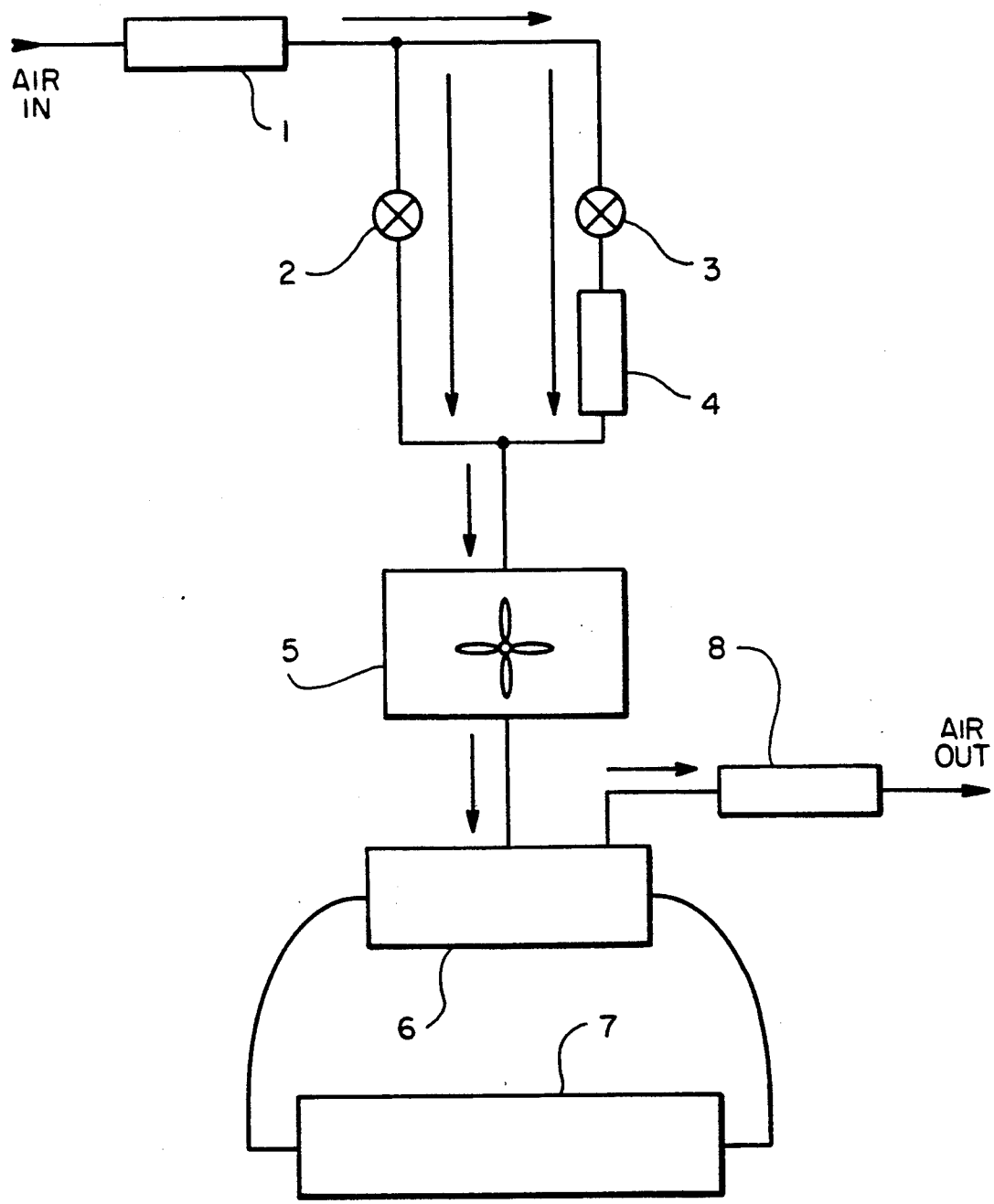
FIG_1

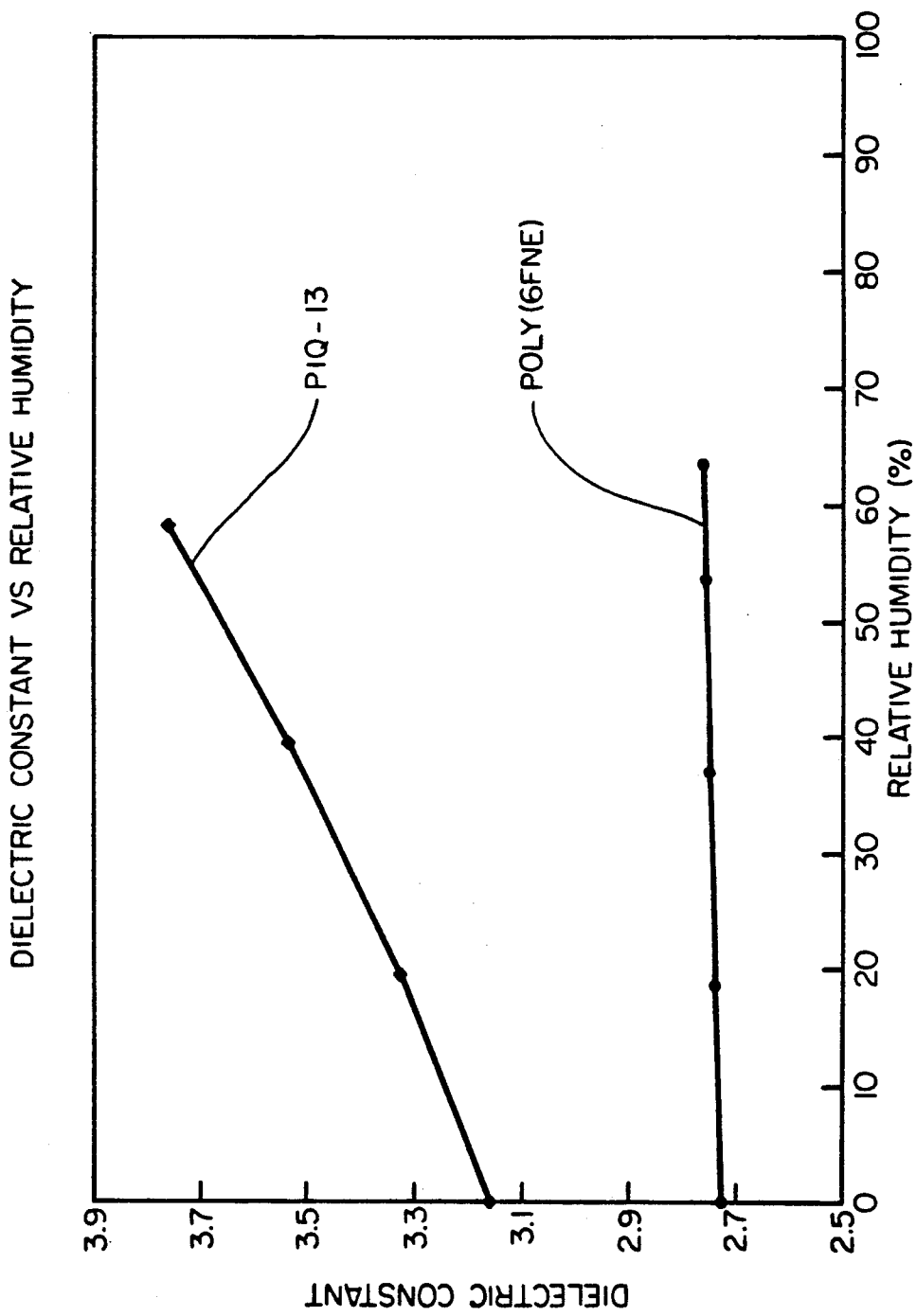

MULTILAYER ELECTRONIC CIRCUIT ARTICLE HAVING A POLY(NAPHTHYL ETHER) DIELECTRIC

BACKGROUND OF THE INVENTION

This invention relates to novel fluorinated poly(naphthyl ethers), cured compositions and multilayer electronic circuit articles comprising the same, and methods therefor.

Polymer films and coatings are often used in the electronic industry, especially in multilayer integrated circuit devices, as insulating materials and passivation layers. Polymers having a low dielectric constant $\epsilon$ are preferred, because components insulated with them can be designed with higher circuit densities and can operate at higher speeds and with less signal broadening. The effect of $\epsilon$ on the performance of multilayer integrated circuit articles is discussed in "Microelectronics Packaging Handbook," Tummala et al (eds.), pp. 687-692 (van Nostrand Reinhold); Watari et al., U.S. Pat. No. 4,744,007 (1988); and Budde et al., U.S. Pat. No. 4,732,843 (1988).

Polyimide is an insulator of choice for many electronic applications, because of its superior mechanical and thermal properties and its fabricability into thin films and coatings. However, polyimide has a relatively high $\epsilon$, a limitation accentuated by polyimide's tendency to absorb water (up to 3-4% in humid environments. Water absorption causes $\epsilon$ to rise, compromising performance. One commercially available polyimide has an $\epsilon$ of about 3.2 at 0 % relative humidity (% RH), which rises to about 3.8 at 60 % RH. As noted by Denton et al. in *J. Electronic Mater.* 14(2), 119 (1985), polyimide moisture absorption can also adversely affect performance through increased insulator conductivity, loss of adhesion, or corrosion. Further, some polyimides are susceptible to hydrolysis and/or attack by solvents (often manifested by crazing or cracking upon exposure to a solvent).

It has been proposed, in Mercer, U.S. Pat. No. 4,835,197 (1989), to improve the solvent resistance of polyimide by curing with an acetylene, maleimide, or vinyl terminated curing agent. However, a polyimide so cured would still have the relatively high dielectric constant of polyimides and their tendency to absorb moisture.

For the aforementioned reasons, it is desirable to develop polymers which have superior high temperature properties, outstanding hydrolytic and solvent resistance, low dielectric constant, and low moisture absorption. The polymers of this invention achieve these objectives.

SUMMARY OF THE INVENTION

This invention provides a fluorinated poly(naphthyl ether) (FPNE) comprising a repeat unit of the formula

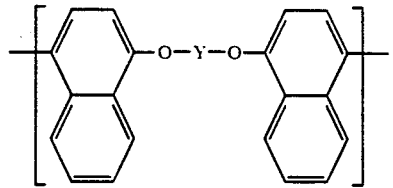

wherein Y is $(CF_2)_m$,

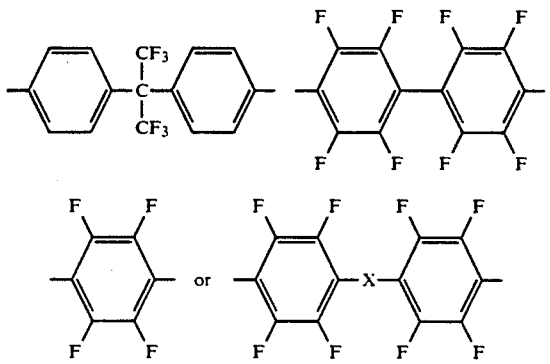

m is an integer from 1 to 4, inclusive, and X is S, CO, $SO_2$, O, $P(C_6H_5)$, or C(OH)H. In a preferred embodiment, FPNE is crosslinked by a bisacetylene crosslinking agent.

This invention also provides a multilayer electronic circuit article comprising (a) a substrate, (b) a plurality of layers of an insulating material on a surface of the substrate, and (c) at least one layer of a conductive material interposed between adjacent layers of the insulating material; the insulating material comprising FPNE.

BRIEF DESCRIPTION OF THE DRAWING(S)

FIG. 1 shows schematically an apparatus for measuring $\epsilon$ of thin films of FPNE's.

FIG. 2 compares the effect of % RH on the $\epsilon$'s of a FPNE and a prior art polymer.

DESCRIPTION OF THE PREFERRED EMBODIMENTS

FPNE's can be prepared by polymerizing a monomer

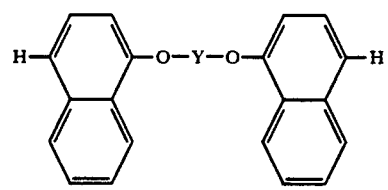

wherein Y is $(CF_2)_m$,

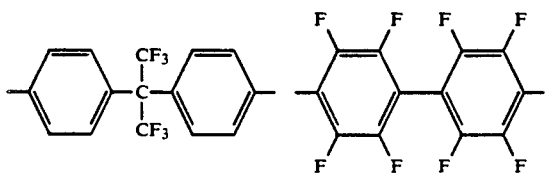

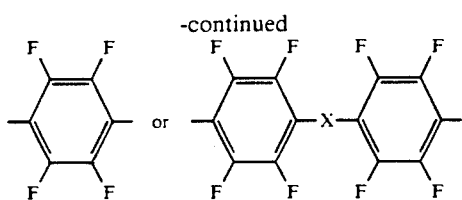

m is an integer from 1 to 4, inclusive, and X is S, CO, SO$_2$, O, P(C$_6$H$_5$), or C(OH)H.

FPNE's can be homopolymers consisting essentially of a single one of the aforementioned repeat units. They can also be copolymers comprising two or more of the above repeat units, or even a copolymer comprising an FPNE repeat unit in combination with a different kind of repeat unit, the copolymer comprising preferably at least 60 mole %, more preferably at least 80 mole % FPNE repeat units. FPNE's preferably have a viscosity of at least 500 cp, more preferably at least 1000 cp, measured at 20% solids in diethyl benzene using a Brookefield viscometer.

The monomers are polymerized in an oxidative coupling (dehydrogenation) reaction in the presence of a catalyst. Preferred catalysts are ferric chloride and cupric chloride. A preferred solvent is nitrobenzene, which also acts as the oxidant for the coupling reaction. Mixtures of nitrobenzene with other, inert solvents may be used. Typically, the polymerization is conducted in the presence of an excess of catalyst, at least 2 moles (and preferably 3 moles) per mole of monomer, at about 25° C. for 16-24 hr. Such reactions are described in detail in Percec et al., U.S. Pat. No. 4,806,617 (1989), the disclosure of which is incorporated herein by reference.

The monomers can be synthesized by condensing two equivalents of a 1-halonaphthalene with one equivalent of a diol HO-Y-OH, for example 1-bromonaphthalene with 4,4'-(hexafluoroisopropylidene)diphenol, also known as bisphenol F. Alternatively, two equivalents of 1-naphthol are condensed with a dihalide Z-Y-Z (where Z is halogen), for example hexafluorobenzene. Where Z-Y-Z is a polyfluorinated aromatic compound such as hexafluorobenzene and decafluorobiphenyl, generally only two fluorines are displaced, at the 1,4- and 4,4'-positions, respectively.

FPNE's can be crosslinked with various crosslinking agents. A preferred crosslinking agent is a bis-acetylene terminated compound or oligomer, such as

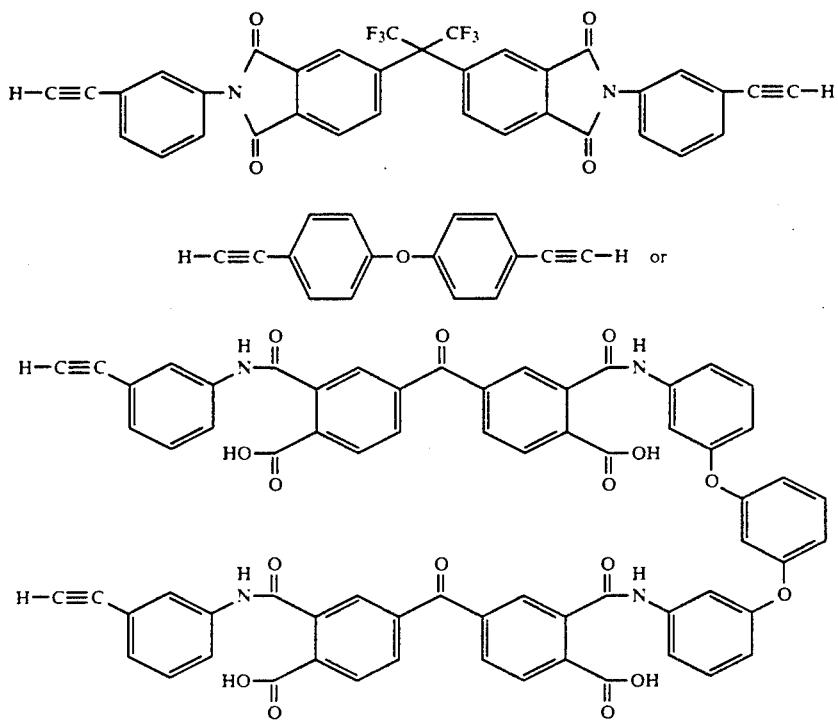

The latter crosslinking agent is known by the tradename Thermid LR-600 and is available commercially from National Starch. Additional bis-acetylene crosslinking agents are disclosed in Mercer, U.S. Pat. No. 4,835,197 (1989), the disclosure of which is incorporated herein by reference.

When crosslinking with a bis-acetylene compound, the FPNE and the crosslinking agent are mixed in the preferred proportions of about 5 to about 50 wt. %, more preferably about 10 to about 25 wt %, of the bis-acetylene compound and then heated to a temperature in the range of 180° to 400° C., preferably 250°-350° C., for 30 min to 3 hr (complex or staged heating schedules may be used). Alternatively, radiation curing may be effected. The mixing can be accomplished by any convenient technique, such as with a two-roll mill, a Brabender or Banbury internal mixer, or a twin-screw extruder. Films or coatings of FPNE mixed with the crosslinking agent can also be prepared by precipitation from a solvent, solution casting, and the like. A preferred method is solution mixing, followed by spin coating onto a substrate to form a thin film or coating which is then cured.

The effect of humidity on the dielectric constant $\epsilon$ of FPNE films can be measured as follows. First, $\epsilon$ in dry air is measured by placing the film in a parallel plate capacitor test cell containing a medium of known dielectric constant and measuring the change in capacitance after the film is inserted. A suitable cell has gold plated capacitor electrodes one inch in diameter and space about 50μ apart. The electrodes are mounted in an insulated brass chamber, for grounding and protection from electromagnetic interference. FPNE film 10–30μ thick and about 1.5×1.5 in. square are used. Measurements are done using two different media, dry air and heptane. $\epsilon$ is calculated according to the following equation:

$$\epsilon = \frac{1.923\, C_2(C_4 - C_3) + 1.0006\, C_3(C_2 - C_1)}{C_2(C_4 - C_3) + C_3(C_2 - C_1)}$$

where $C_1$ is the capacitance of the heptane, $C_2$ is the capacitance of the film in heptane, $C_3$ is the capacitance of the film in dry air, and $C_4$ is the capacitance of dry air. By replacing the dry air with humid air of known % RH, the variation in the FPNE film's $\epsilon$ as a function of % RH can be determined. The dielectric constant $\epsilon'$ of the film in humid air can be calculated by the following equation:

$$\epsilon' = \frac{1.0006\, \epsilon\, C_5(C_3 - C_4)}{\epsilon\, C_4(C_3 - C_5) + 1.0006\, C_3(C_5 - C_4)}$$

where $\epsilon$, $C_3$, and $C_4$ have their previously stated meanings, while $C_5$ is the capacitance of the film in humid air. Typically, $\epsilon$ is measured at 0, 20, 40, and 60% RH. The measurements are made after the film has been permitted to equilibrate for about one day. This method provides a method of measurement which is quick and independent of film thickness. Since both the films and solvents can pick up water from the atmosphere, leading to unstable readings, it is recommended that the measurement apparatus be placed inside a glove bag or a dry box filled with dry nitrogen.

FIG. 1 shows schematically an apparatus suitable for the aforementioned measurements. Inflowing air is passed through a drying chamber 1 and partitioned between two mass flow controllers 2 and 3 (e.g., Porter Series 200F controlllers with 2L/min full scale flow). Air flowing through the branch controlled by controller 3 is moistened by water chamber 4. Air from the two branches is recombined in turbulent flow chamber 5 and thence passed into parallel-plate dielectric cell 6. The capacitance of cell 6 is measured by sensor 7 (e.g., a GenRad 1688 LC Digi-Bridge). The relative humidity of the air is measured by dew point hydgrometer 8 (e.g., General Eastern System 1100DP). Cell 6 is of the type described hereinabove.

The $\epsilon$ of FPNE films also can be measured by alternative techniques which however are less convenient because they require the determination of the thickness of the film. Such techniques are described in Denton et al., cited supra, and Stoakley et al., SAMPE Q., Oct. 1989, pp. 3–6.

FPNE's can be fabricated into shaped articles by conventional techniques, depending on the desired shape. Films or coatings can be formed by extrusion, spraying, spin coating, or casting, with solution processes being preferred. Fibers can be formed by melt spinning or like methods. Preferred solvents for solution processes are aromatic hydrocarbons such as toluene, xylene, diethylbenzene and chlorinated solvents such as chloroform, methylene chloride and the like. Other shapes may be prepared by injection, compression, pour, or blow molding or the like.

Additives can be used to enhance or impart particular target properties, as is conventionally known in the polymer art, including stabilizers, flame retardants, pigments, plasticizers, surfactants, and the like. Compatible or non-compatible polymers can be blended in to give a desired property.

FPNE's are useful as adhesives, coatings (especially semiconductor coatings for alpha-particle barriers, passivation, and mechanical protection), and matrix resins for fiber reinforced composites. They are particularly useful for the preparation of a multilayered article in electronic systems. The article comprises a substrate, for example, silicon, glass or ceramic, with at least one layer of FPNE (preferably cured) deposited on a surface thereof. Generally a plurality of layers are successively deposited and cured. One of more layers of conductive material can be interposed between two adjacent layers of the FPNE. The conductive layer(s) are generally not coextensive with the FPNE layers and typically form a plurality of electrically conductive pathways. The conductive layer(s) are preferably of metal, but can comprise a semiconductive material.

FPNE's have superior high temperature performance properties ($T_g$ above 200° C.), hydrolytic resistance, low water absorption (generally less than 1% and often less than 0.2% after contact with 50° C. water for 16 hr), and a low dielectric constant (generally less than 3.5 and often less than 3), even in humid environments such as 60% RH air.

A multilayer article can be prepared by coating the FPNE (along with the crosslinking agent) from solution, preferably by spin coating, onto the substrate. The solvent is evaporated and the polymer is cured at an elevated temperature appropriate for the particular crosslinking agent being used. Typically the coating thickness is about 5 to about 40 microns. A conductive layer is applied over the FPNE layer, using for example a sputtering technique with the appropriate areas masked to create the desired conductive pathways. The next FPNE layer is then applied in the same manner. These steps can be repeated until the desired multi-layer article is produced. The multilayered article can be used as a packaging-interconnect device for integrated circuits.

The practice of this invention can be further understood by reference to the following examples, which are provided by means of illustration, not limitation.

EXAMPLE 1

This example describes the preparation of the monomer 2,2-bis(4-(1-naphthoxy)phenyl)hexafluoropropane (6FNE). A 500 mL three neck round bottom flask equipped with nitrogen inlet, thermometer, overhead stirrer, and condenser was charged with 4,4'-(hexafluoroisopropylidene)diphenol (24.5 g, 0.0729 mole), 1-bromonaphthalene (31.0 g, 0.150 mole), potassium carbonate (21.9 g, 0.162 mole), copper (I) iodide (0.8 g), and N,N-dimethylacetamide (DMAc, 375 mL). The reaction mixture was purged with nitrogen for 10 min and then heated, with stirring, at about 150° C. under nitrogen for 5 days. The mixture was cooled to room temperature and filtered. About 250 mL of DMAc was removed by distillation at reduced pressure. The mixture was added to 250 mL of toluene/hexane (80/20) and washed twice with 20% sodium hydroxide (2×150 mL) and distilled water (2×150 mL). The toluene/hexane layer was dried over magnesium sulfate, filtered, and concentrated under reduced pressure to yield a brown oil (38.4 g), which partially crystallized on standing at room temperature overnight. The product was suspended in a 50/50 ethanol/methanol mixture and filtered to yield an off-white crystalline solid (m.p. 94°–95° C.). The yield was 34.2 g (79.8%). The structure of 6FNE was confirmed by H-1 and C-13 NMR and GC/MS (m+/e=588).

EXAMPLE 2

This example describes the polymerization of 6FNE. A 100 mL round bottom flask was purged with nitrogen and charged with 6FNE (3.6 g, 0.0061 mole) and nitrobenzene (25 mL, dried over 3Å molecular sieves). Anhydrous ferric chloride (2.96 g, 0.0183 mole) was added portionwise over 15 min. The reaction mixture was stirred under nitrogen at room temperature for 4 hr and then poured into rapidly stirred methanol to precipitate the polymer. The polymer was collected by filtration and washed twice with hot methanol (2×70 mL). Poly(6FNE), having a repeat unit

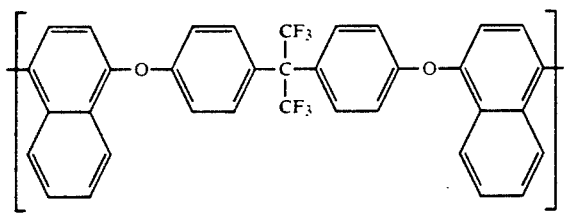

was obtained as a light tan powder (yield 3.2 g, 89%). The polymer was a thermoplastic material which could be compression molded into thin films at 660° F. (349° C.). Its $T_g$ was 247° C. by DSC. The polymer was soluble in toluene, 1-methyl-2-pyrrolidone (NMP), and tetrahydrofuran (THF). A thin film of the polymer showed a bulk moisture absorption of 0.15% after immersion in 50° C. water for 16 hr.

EXAMPLE 3

The monomer 4,4'-bis(1-naphthoxy)octafluorobiphenyl (8FNE) was prepared by the following procedure. A 100 mL round bottom flask was charged with decafluorobiphenyl (3.01 g, 0.0090 mole), 1-naphthol (2.60 g, 0.0181 mole), potassium carbonate (2.95 g, 0.0218 mole), and DMAc (40 g). The mixture was heated with stirring at about 140° C. for 2 hr and then cooled to room temperature, filtered, and poured into toluene (100 mL). The toluene solution was washed with 5% sodium hydroxide (50 mL) and then twice with deionized water (2×100 mL). After drying with magnesium sulfate and filtering, it was concentrated by rotary evaporation to yield a red solid. The solid was recrystallized from DMAc/water, filtered, and dried to yield 8FNE (3.9 g, 78.8% yield; m.p. 189°–191° C.; GC/MS m+/e 582).

EXAMPLE 4

8FNE was polymerized by the method of Example 2, except that 8FNE (3.4 g, 0.0061 mole) was used instead of the 6FNE. Poly(8FNE) was obtained as an off-white powder (3.1 g, 90% yield). It had the repeat unit

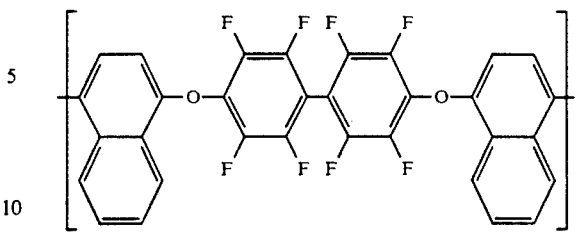

Poly(8FNE) had an infrared absorption at 1240 cm$^{-1}$ (C-O-C) and a $T_g$ of 281° C. by DSC.

EXAMPLE 5

The monomer 1,4-bis(1-naphthoxy)tetrafluorobenzene (4FNE) was prepared as follows. A 100 mL round bottom flask equipped with a magnetic stirrer was charged with hexafluorobenzene (3.53 g, 0.0190 mole), 1-naphthol, and DMAc (50 mL). After the solids dissolved, potassium carbonate (6.50 g, 0.048 mole) was added and the mixture was heated at about 140° C. for 2 hr. The mixture was then cooled to room temperature, filtered, and poured into toluene (150 mL). The toluene solution was washed twice with water (2×150 mL) and concentrated by rotary evaporation to yield an off-white powder (7.91 g). Analysis of the powder by GC showed a mixture of isomers (2% ortho, 8% meta, and 90% para). The powder was recrystallized from a mixture of N,N-dimethylformamide (DMF) and water to yield the desired all-para 4FNE, GC/MS (m+/e 434).

EXAMPLE 6

4FNE was polymerized by the procedure of Example 2, except that 4FNE (2.65 g, 0.0061 mole) was used instead of 6FNE. Poly(4FNE) was obtained as a light tan powder (2.3 g, 87% yield) It had a repeat unit

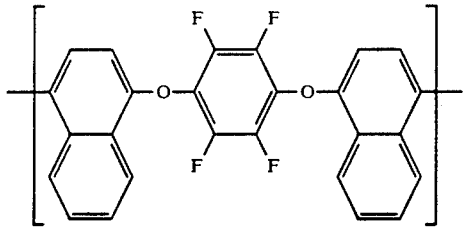

Poly(4FNE) had an infrared absorption at 1240 cm$^{-1}$ (C-O-C). Its intrinsic viscosity was 0.39 dL/g at 25° C. in THF. It was melt fusible and could be compression molded into thin films at 660° F. (349° C.).

EXAMPLE 7

A copolymer of 6FNE and 8FNE was synthesized as follows. A mixture of 6FNE (1.1 g, 0.0019 mole) and 8FNE (1.10 g, 0.002 mole) was copolymerized and isolated generally following the procedure of Example 2. The copolymer had a $T_g$ of 276° C. by DSC and an intrinsic viscosity of 0.34 at 25° C. in THF. It was melt fusible and was compression molded into thin films at 700° F. (371° C.). The film showed a bulk moisture absorption of 0.1% after immersion in 50° C. water for 16 hr.

EXAMPLE 8

In this comparative example, a fluorinated polyimide (FPI) is prepared and compared against FPNE's for moisture absorption properties. A 100 mL round bottom flask was charged with 4,4'-bis(4-aminophenoxy)-biphenyl (3.35 g, 0.009 mole) and NMP (17 g). After stirring at room temperature under nitrogen for 45 min, a solution of 2,2'-bis(3,4-dicarboxyphenyl)hexafluoropropane dianhydride (4.00 g, 0.009 mole) in NMP (14 mL) was added dropwise with stirring over 10 min. After stirring for an additional 24 hr at room temperature, a viscous solution (2400 cps) resulted. The solution was spin coated onto a 4×4 in (10.16×10.16 cm) glass substrate at 2000 rpm and dried 30 min at 100° C., then 20 min at 200° C., and 30 min at 350° C. to yield an amber film of a fluorinated polyimide having the repeat unit

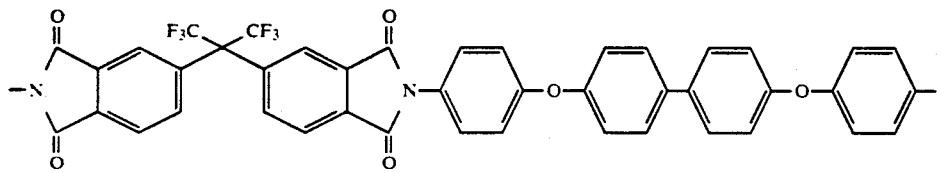

The film showed a bulk moisture absorption of 0.85% after immersion in 50° C. water for 16 hr.

EXAMPLE 9

This is another comparative example in which the moisture absorption properties of a commercially available polyimide (PIQ-13, from Hitachi) was compared against those for FPNE's.

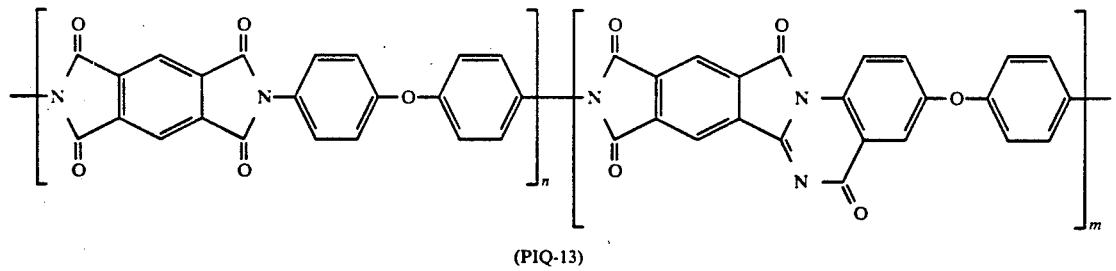

(PIQ-13)

A sample of the poly(amic acid) precursor of PIQ-13 was coated onto a glass substrate and dried as described in Example 8 above, to yield an amber film. This film showed a bulk moisture absorption of 2.55% after immersion in 50° C. water for 16 hr. FIG. 1 compares the dielectric constant of PIQ-13 and poly(6FNE) as a function of relative humidity (% RH).

The properties of poly(6FNE) and the copoly(6FNE-8FNE) of Example 7 are compared against the polyimides of Examples 8 and 9 in Table I. As the results show, the polymers of this invention have superior electrical properties lower dielectric constant, lesser changes in the dielectric constant as a function of relative humidity (% RH), and lower moisture absorption upon exposure to water. These ar all advantageous properties in electronic circuitry protection and packaging applications.

TABLE I

Comparison of Effect of Relative Humidity on Properties of PFNE's and Polyimides

| Polymer | Dielectric Constant | | | Moisture Absorption (%)* |
|---|---|---|---|---|
| | at 0% RH | at 60% RH | % Change, 0 to 60% RH | |
| PIQ-13 | 3.16 | 3.76 | 19.0 | 2.55 |
| FPI | 2.85 | 3.22 | 11.6 | 0.85 |
| Poly (6FNE) | 2.72 | 2.75 | 1.1 | 0.15 |
| Copoly (6FNE-8FNE) | — | — | — | 0.10 |

*After 16 hr immersion in 50° C. water.

EXAMPLE 10

This example illustrates the crosslinking of poly(6FNE) to improve its solvent resistance properties. The acetylene-terminated diimide

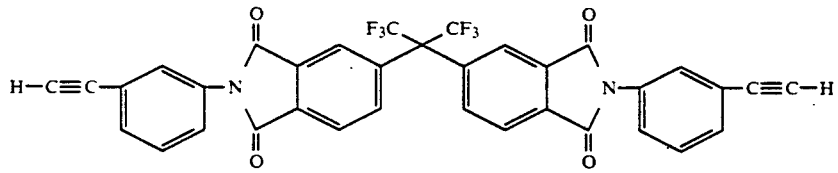

was prepared as follows. A 100 mL round bottom flask was charged with 3-aminophenylacetylene (2.00 g, 0.017 mole) and DMAc (50 mL), followed by 4,4'-(hexafluoroisopropylidene)bis(phthalic anhydride). The mixture was stirred at room temperature for 1 hr, followed by heating at 150° C. for 3 hr. The mixture was then cooled back to room temperature and poured into water (125 mL). The resulting solid precipitate was filtered, washed with 50/50 water/ethanol mixture, and dried to yield the above diacetylene diimide as a light tan solid which was used without further purification.

A solution of poly(6FNE) (4.0 g) and the above diacetylene diimide (1.0 g) in diethylbenzene (20 mL) was spin coated onto a ceramic substrate and heated according to the following staged schedule: 20 min/100° C., 20 min/180° C., and 30 min/400° C. An uniform coating of cured poly(6FNE) which was insoluble in diethylbenzene was obtained. The coating was resistant to solvent stress-cracking—when a second layer of poly(6FNE) was spin coated over it, it did not crack, although diethylbenzene will crack films of uncrosslinked poly(6FNE).

EXAMPLE 11

This example illustrates the crosslinking of poly(6FNE) by the acetylene terminated ether

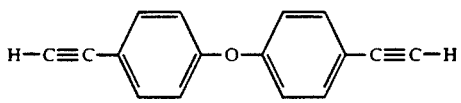

4,4'-Diacetylene diphenyl ether (DADPE) was prepared as follows. A 250 mL round bottom flask was charged with 4,4'-dibromophenylether (25 g, 0.076 mole), dichlorobis(triphenylphosphine) palladium (0.2 g), triphenylphosphine (0.4 g), copper (I) iodide (0.1 g), 2-methyl-3-butyn-2-ol (20 g, 0.24 mole), triethyl amine (100 mL), and pyridine (25 mL). The reaction mixture was purged with nitrogen and then heated at about 80° C. (still under nitrogen) for 20 hr. The mixture was cooled to room temperature and filtered to remove the hydrobromide salts formed during the reaction. The mixture was concentrated in vacuo to yield a yellow oil which crystallized upon standing. The solid was recrystallized from toluene/hexane and dried to yield the diacetone adduct precursor to DADPE

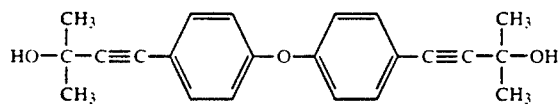

as a white crystalline solid (14.7 g), m.p. 133°–134° C., GS/ms m+/e 334.

The diacetone adduct precursor (5.50 g, 0.0165 mole) was added to a 250 mL round bottom flask, along with toluene (100 mL) and 10% methanolic potassium hydroxide (50 mL). The mixture was heated to reflux and about 40 mL of solvent was removed by distillation. The mixture was then heated at reflux for another 2 hr. The solution was cooled to room temperature, filtered through Celite, washed with water (50 mL), and concentrated in vacuo. The residue was redissolved in hexane (50 mL), filtered through alumina, dried over magnesium sulfate, filtered, and concentrated again to yield DADPE as a white crystalline solid (3.10 g, m.p. 71°–73° C.).

An aliquot (2 mL) of a solution of poly(6FNE) (2.0 g) and DADPE (0.5 g) in diethylbenzene (10 mL) was spin coated onto a glass substrate and cured by the schedule of Example 10 to produce a transparent film. This film did not crack when exposed to diethylbenzene.

What is claimed is:

1. A multilayer electronic circuit article comprising (a) silicon, glass, or ceramic substrate, (b) a plurality of layers of an insulating material on a surface of the substrate, and (c) at least one layer of a conductive material selected from the group consisting of metals and semiconductive materials, interposed between adjacent layers of the insulating material; the insulating material comprising a fluorinated poly(naphthyl ether) comprising a repeat unit of the formula

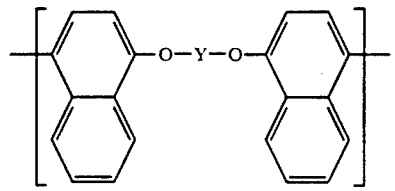

wherein Y is $(CF_2)_m$,

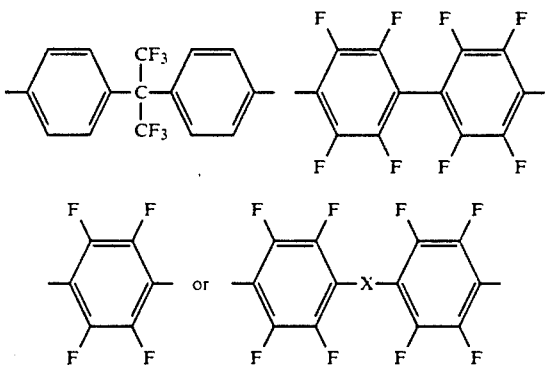

m is an integer from 1 to 4, inclusive, and X is S, CO, $SO_2$, O, $P(C_6H_5)$, or C(OH)H.

2. A multilayer article according to claim 1, wherein the fluorinated poly(naphthyl ether) has been crosslinked.

3. A multilayer electronic circuit article according to claim 1, wherein the fluorinated poly(naphthyl ether) has been crosslinked with a bisacetylene crosslinking agent.

4. A multilayer electronic circuit article according to claim 1, wherein the fluorinated poly(naphthyl ether) has been crosslinked with a bis-acetylene crosslinking agent selected from the group consisting of

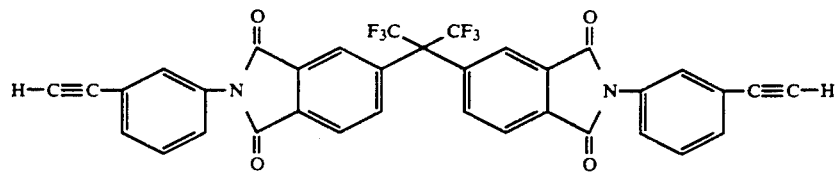

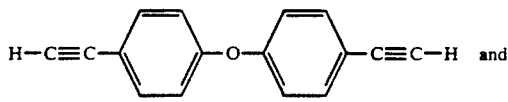 and

-continued

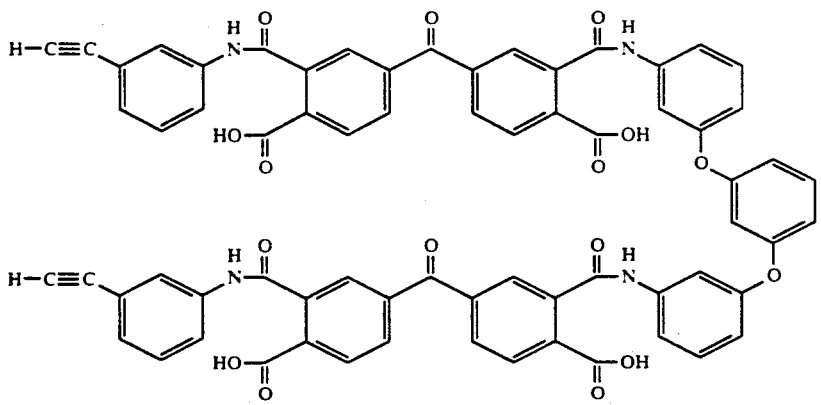

5. A multilayer article according to claim 1 or 4, wherein Y in the fluorinated poly(naphthyl ether) is

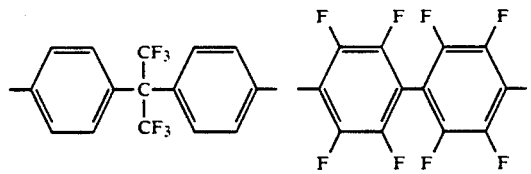

or

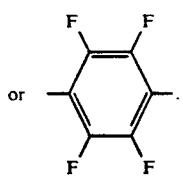

6. A multilayer electronic circuit article according to claim 1 or 4, wherein the fluorinated poly(naphthyl ether) comprises a repeat unit of the formula

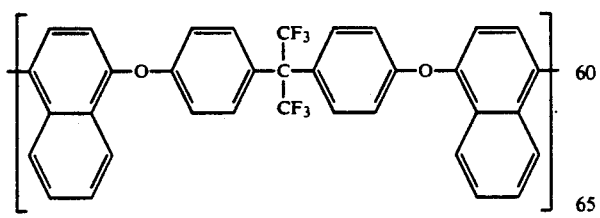

7. A multilayer article according to claim 1 or 4, wherein the fluorinated poly(naphthyl ether) comprises a repeat unit of the formula

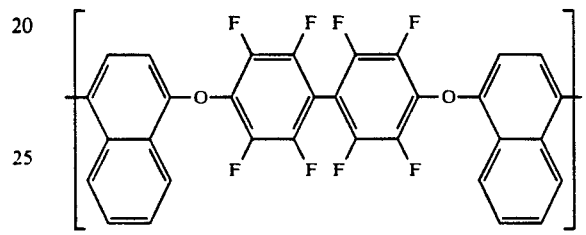

8. A multilayer article according to claim 1 or 4, wherein the fluorinated poly(naphthyl ether) comprises a repeat unit of the formula

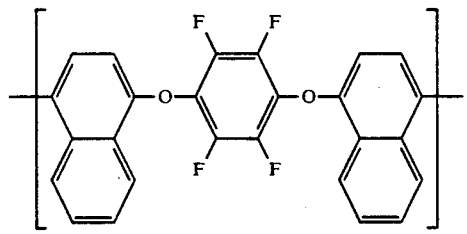

9. A multilayer article according to claim 1 or 4, wherein the fluorinated poly(naphthyl ether) is a copolymer comprising repeat units of the formula

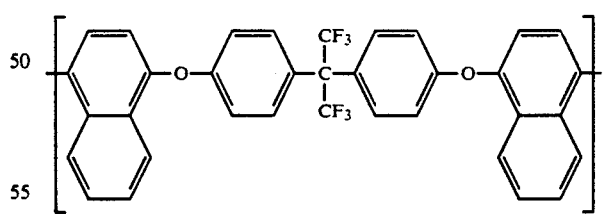

and

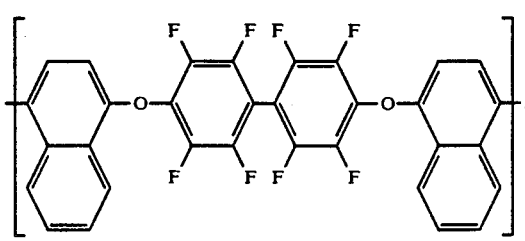

* * * * *